United States Patent
Malouf et al.

(10) Patent No.: US 11,273,278 B2
(45) Date of Patent: *Mar. 15, 2022

(54) METHODS AND APPARATUS FOR PREVENTING RAINOUT

(71) Applicant: ResMed Pty Ltd, Bella Vista (AU)

(72) Inventors: Gordon Joseph Malouf, Sydney (AU); Liam Holley, Marrickville (AU); Paul Jan Klasek, Bonnyrigg Heights (AU)

(73) Assignee: ResMed Pty Ltd

( * ) Notice: Subject to any disclaimer, the term of this patent is extended or adjusted under 35 U.S.C. 154(b) by 429 days.

This patent is subject to a terminal disclaimer.

(21) Appl. No.: 16/108,839

(22) Filed: Aug. 22, 2018

(65) Prior Publication Data

US 2018/0361100 A1 Dec. 20, 2018

Related U.S. Application Data

(63) Continuation of application No. 13/820,620, filed as application No. PCT/AU2011/001137 on Sep. 2, 2011, now Pat. No. 10,076,628.

(30) Foreign Application Priority Data

Sep. 6, 2010 (AU) ................ 2010903971

(51) Int. Cl.
*A61M 16/08* (2006.01)
*A61M 16/20* (2006.01)
(Continued)

(52) U.S. Cl.
CPC .... *A61M 16/0808* (2013.01); *A61M 16/0057* (2013.01); *A61M 16/04* (2013.01);
(Continued)

(58) Field of Classification Search
CPC ............ A61M 16/109; A61M 16/0051; A61M 16/16; A61M 2039/0646;
(Continued)

(56) References Cited

U.S. PATENT DOCUMENTS 3,225,758 A 12/1965 Morch
4,621,632 A * 11/1986 Bartels .............. A61M 16/1085
128/203.27

(Continued)

FOREIGN PATENT DOCUMENTS

CN 101622050 A 1/2010
EP 1935446 A1 6/2008
(Continued)

OTHER PUBLICATIONS

European Search Report for Application No. EP11822923 dated Aug. 17, 2015.
(Continued)

*Primary Examiner* — Victoria Murphy
(74) *Attorney, Agent, or Firm* — Botos Churchill IP Law LLP

(57) ABSTRACT

Components for a respiratory treatment apparatus that is capable of providing a humidified respiratory treatment permit a reduction in condensation in a patient interface and/or its gas delivery tubing. In some embodiments, a rainout valve that may be an integrated component of a humidifier output aperture, or coupled thereto, may reduce condensation with a vapor barrier operable to selectively block and permit humidified gas transfer from the humidifier. For example, the barrier may be operable to open in response to a flow of pressurized breathable gas that may be generated by a flow generator of the respiratory treatment apparatus. In the absence of such a generation of pressurized flow, the barrier may prevent a transfer of the humidified gas
(Continued)

such as into a conduit for a patient interface by retracting to a closed position. Example vapor barriers may include a resilient membrane, cover, bellows, flap, shutter or other suitable valve.

25 Claims, 15 Drawing Sheets

(51) Int. Cl.
*A61M 16/00* (2006.01)
*A61M 16/04* (2006.01)
*A61M 16/06* (2006.01)
*A61M 16/12* (2006.01)
*A61M 16/16* (2006.01)

(52) U.S. Cl.
CPC .... *A61M 16/0666* (2013.01); *A61M 16/0683* (2013.01); *A61M 16/0833* (2014.02); *A61M 16/0875* (2013.01); *A61M 16/20* (2013.01); *A61M 16/202* (2014.02); *A61M 16/208* (2013.01); *A61M 16/12* (2013.01); *A61M 16/16* (2013.01); *A61M 2202/025* (2013.01); *A61M 2202/0208* (2013.01); *A61M 2202/0266* (2013.01)

(58) Field of Classification Search
CPC .. A61M 2039/0666; A61M 2039/2473; A61M 39/00; A61M 39/02; A61M 39/0247; A61M 39/16; A61M 39/227; A61M 39/24; A61M 5/16881; A61M 16/10; A61M 16/1045; A61M 16/1075; A61M 16/108; A61M 16/1085; A61M 16/20; A61M 16/204; A61M 16/205; A61M 16/206; A61M 16/207; A61M 16/209; A61M 16/208

USPC ....................................... 128/205.24, 203.11
See application file for complete search history.

(56) References Cited

U.S. PATENT DOCUMENTS

| | | |
|---|---|---|
| 4,858,605 A | 8/1989 | Levy |
| 5,647,355 A | 7/1997 | Starr et al. |
| 5,704,345 A | 1/1998 | Berthon-Jones |
| 5,896,857 A * | 4/1999 | Hely ....................... A62B 9/02 |
| | | 128/203.11 |
| 6,189,532 B1 | 2/2001 | Hely et al. |
| 6,240,921 B1 | 6/2001 | Brydon |
| 6,588,421 B1 * | 7/2003 | Diehl .................... A61M 16/12 |
| | | 128/201.13 |
| 6,595,212 B1 | 7/2003 | Arnott |
| 9,903,371 B2 | 2/2018 | Row |
| 2004/0016432 A1 | 1/2004 | Genger et al. |
| 2006/0076017 A1* | 4/2006 | Walker ............. A61M 16/0683 |
| | | 128/205.24 |
| 2007/0132117 A1* | 6/2007 | Pujol .................... A61M 16/16 |
| | | 261/119.1 |
| 2007/0157928 A1 | 7/2007 | Pujol et al. |
| 2008/0072900 A1 | 3/2008 | Kenyon |
| 2010/0147302 A1 | 6/2010 | Selvarajan et al. |

FOREIGN PATENT DOCUMENTS

| | | |
|---|---|---|
| JP | 2005-066072 A | 3/2005 |
| WO | 2010031126 A1 | 3/2010 |
| WO | 2010141983 A1 | 12/2010 |

OTHER PUBLICATIONS

International Search Report for Application No. PCT/AU2011/001137 dated Nov. 11, 2011.

* cited by examiner

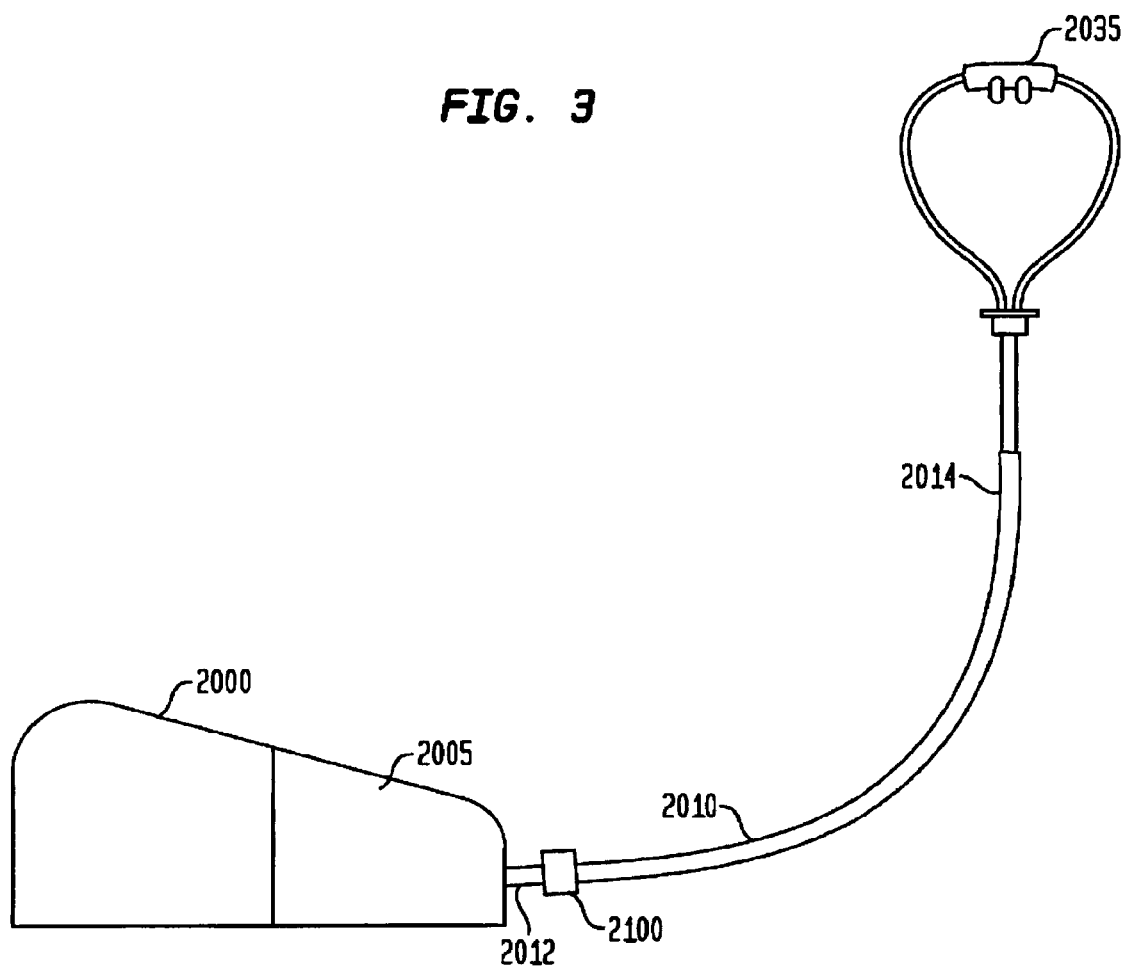

METHODS AND APPARATUS FOR PREVENTING RAINOUT

CROSS REFERENCE TO RELATED APPLICATIONS

The present application is a continuation of U.S. patent application Ser. No. 13/820,620, filed on Mar. 4, 2013, which application is a national phase entry under 35 U.S.C. § 371 of International Application No. PCT/AU2011/001137, filed Sep. 2, 2011, which claims priority from Australian Provisional Patent Application No. 2010903971, filed Sep. 6, 2010, all of which are incorporated herein by reference.

FIELD OF THE TECHNOLOGY

The present technology relates to methods and apparatus for preventing condensation or rainout in conduits or devices attached to all forms of humidifier systems, such as a humidified respiratory treatment apparatus. Such apparatus may provide respiratory pressure treatment including, for example, invasive and non-invasive ventilation, Continuous Positive Airway Pressure (CPAP), Bilevel therapy, high flow therapy and treatment for sleep disordered breathing (SDB) conditions such as Obstructive Sleep Apnea (OSA), and for various other respiratory disorders and diseases such as respiratory insufficiency, asthma and Chronic Obstructive Pulmonary Disease (COPD). Embodiments of the technology may help to reduce the rainout in respiratory air delivery conduits attached to humidifier systems.

BACKGROUND OF THE TECHNOLOGY

Respiratory treatment apparatus commonly include means to alter the humidity of a provided breathable gas in order to reduce drying of the patient's airway and consequent patient discomfort and associated complications. The use of a humidifier placed between the flow generator of such an apparatus and the patient interface, produces humidified gas that minimizes drying of the nasal mucosa and increases patient airway comfort. The humidifier is generally placed between the flow generator and the air delivery conduit, with the air delivery conduit being attached to the patient interface unit.

As schematically shown in FIG. 1, a respiratory treatment apparatus, for example a Continuous Positive Airway Pressure (CPAP) system, generally includes a positive airway pressure (PAP) device 2000 with a flow generator, a humidifier 2005, an air delivery conduit 2010 (also referred to as a tube or tubing), and a patient interface 2030. The air delivery conduit 2010 is coupled to the outlet 2012 of the humidifier 2005. In use, the respiratory device 2000 generates a supply of pressurized air that is humidified by the humidifier 2005 and delivered to the patient via an air delivery conduit 2010 that includes one end coupled to the outlet 2012 of the humidifier 2005 and an opposite end coupled to the inlet 2014 of the patient interface 2030. The patient interface comfortably engages the patient's face and provides communication with the patient's airways. The patient interface or mask may have any suitable configuration as is known in the art, e.g., full-face mask, nasal mask, oro-nasal mask, mouth mask, nasal prongs, etc. Also, headgear may be utilized to comfortably support the patient interface in a desired position on the patient's face.

Many humidifier types have been proposed, including humidifiers that are either integrated with or configured to be coupled to the relevant respiratory treatment apparatus. While passive humidifiers can provide some relief, generally a heated humidifier is required to provide sufficient humidity and temperature to the air so that patient will be comfortable.

Humidifiers may typically include a water tub having a capacity of several hundred milliliters, a heating element for heating the water in the tub, a control to enable the level of humidification to be varied, a gas inlet to receive gas from the flow generator, and a gas outlet adapted to be connected to a gas conduit that delivers the humidified pressurized gas to the patient's interface unit.

Air delivery conduits are generally used to connect a patient interface to a respiratory humidifier system to enable delivery of the humidified gas flow to the patient. Air delivery conduits are available in a variety of lengths and diameters. For respiratory conduits, a standard tubing may have an external diameter of 22 mm (internal diameter 19 mm) and lengths of 1.8 metres or 2 metres. Smaller conduits or tubing diameters such as 15 mm tubing may be used as described in co-pending U.S. application Ser. No. 12/461,967 filed 28 Aug. 2009, the content of which is incorporated herein in its entirety.

Both unheated and heated air delivery conduits are known to be used with CPAP and ventilation systems. The conduits are generally attached to the outlet of the humidification system at one end and to a patient interface unit at the opposing end. In such humidification systems a common problem can occur with rainout within the air delivery conduit. The humidified air may cool on its path along the conduit from the humidifier to the patient, leading to the phenomenon of "rain-out", or condensation, forming on the inside of the conduit. In use, heated air delivery conduits assist in addressing the issues with rainout or condensation within the conduit. For example, a heated conduit may maintain a desired temperature throughout the heated conduit preventing the cooling of the humidified gas flowing through it during operation of the respiratory treatment apparatus.

However, rainout or condensation may also occur when the system is turned off after use when the humidified air remaining within the system begins to cool. Some systems include or recommend a controlled cool down period for the humidifier and/or the heated conduit to assist in reducing the level of rainout. However, some rainout or condensation still tends to occur within the conduit. The presence of condensation or moisture within the conduits can lead to bacterial or microbial growth within the conduits and hygiene issues.

It may be desirable to develop devices to reduce rainout or condensation within conduits attached to humidification systems such as when humidification is no longer being provided or when the system is turned off.

SUMMARY OF THE TECHNOLOGY

The present technology involves components of a respiratory treatment apparatus capable of providing a humidified breathable gas.

Some embodiments of the present technology may include a vapor barrier for a gas channel of the respiratory treatment apparatus.

Still further embodiments may include such a vapor barrier being operable to selectively permit and prevent a transfer of humidified gas in the gas channel of the respiratory treatment apparatus.

Some embodiments relate to such a vapor barrier being operable for movement to selectively permit and prevent a transfer of humidified gas in response to the presence or absence of a flow of breathable gas generated by the respiratory treatment apparatus.

For example, a device may reduce conduit rainout attributable to a breathable supply of humidified gas by a respiratory treatment apparatus. The device may include a breathable gas conduit having an input aperture and an output aperture. The gas conduit is configured as a channel for movement of a humidified gas between the input aperture and the output aperture. The conduit may further include a vapor barrier in the channel between the input aperture and the output aperture of the gas conduit. The vapor barrier may be operable to selectively permit and prevent vapor to pass from the input aperture to the output aperture.

In some such cases, the vapor barrier may be configured to normally seal the channel to prevent vapor passing from the input aperture to the output aperture. Optionally, the vapor barrier may be configured to open to permit vapor to pass from the input aperture to the output aperture by an application of pneumatic pressure applied at the input aperture that exceeds pressure at the output aperture. Moreover, the vapor barrier may be configured to close to prevent vapor passing from the output aperture to the input aperture with a pneumatic pressure applied at the output aperture that exceeds or is equal to the pressure at the input aperture.

In some such embodiments, the vapor barrier may include a valve flap, such as a valve flap formed of a flexibly resilient material. Optionally, the vapor barrier may be formed as a bellows or a duckbill valve. Still further, the vapor barrier may include an aperture cover and a biasing member or spring.

In some embodiments of such a device, the gas conduit may also include an atmosphere access port. In such a case, the vapor barrier may be configured to cover the atmosphere access port when the vapor barrier permits vapor to pass from the input aperture to the output aperture. Such a vapor barrier may also be configured to uncover the atmosphere access port when the vapor barrier prevents vapor passing from the input aperture to the output aperture.

Optionally, the gas conduit may be configured at the input aperture as a coupling for a humidifier or a humidifier component of a respiratory treatment apparatus. Alternatively, it may be an integrated component of a humidifier. Moreover, the gas conduit may be configured at the output aperture as a coupling for a conduit of a patient interface.

In some embodiments of the present technology, a humidifier includes an outlet that is adapted to be shut off when no pressurized gas flow is travelling through the humidifier and to the outlet.

Certain embodiments relate to a rainout valve adapted to be coupled to an outlet of a humidifier to block or obstruct the transfer of humidified gas from flowing through the valve in the absence of a pressurized flow.

Certain embodiments relate to a valve arrangement adapted to adjustably obstruct an outlet of a humidifier, the valve comprising a first side coupled to the humidifier outlet, a second side adapted to couple to a conduit, and a blocking member that is located between the first side and the second side and is configured to move between a first position and a second position, wherein in the absence of a force being applied through the valve, the blocking member is in the first position and obstructs access from the first side to the second side, and in the presence of a force being applied through the valve the blocking member is adapted to move to a second position to allow access from the first side to the second side. The force may be a pressurized gas flow. The blocking member may be a membrane, a flap, such as a silicone flap, a duckbill valve, or any other type of blocking system. Alternatively the blocking member may be moved between the first position and the second position by a spring action.

In certain embodiments, the valve arrangement may include a supplementary gas supply port adapted to allow connection of a supplementary gas, such as oxygen, into the second side.

Some embodiments of the valve arrangement may also include an aperture to atmosphere, such as on the second end of the valve. The aperture may be configured to be open to atmosphere when the blocking member is in the first position and closed when the blocking member is in the second position. The blocking member may be further configured to obstruct the aperture when in the second position.

Some embodiments involve a humidifier including an inlet and an outlet and including a valve arrangement coupled to the outlet that is adapted to adjustably obstruct the outlet of the humidifier in the absence of a force being applied to the valve. The valve arrangement may be integrated into the outlet of the humidifier.

Certain embodiments relate to a humidifier having a blocking means coupled to the humidifier outlet to prevent humidified gas from leaving the humidifier when there is no pressurized flow through the humidifier.

Certain embodiments relate to a valve arrangement for controlling the opening and closing of a humidifier outlet.

Certain embodiments relate to a rainout valve adapted to be coupled to an outlet of a humidifier and configured to block the transfer of humidified gas from flowing through the valve in the absence of a pressurized flow travelling through the humidifier and to the outlet.

Certain embodiments involve a respiratory PAP system. The system may include a flow generator coupled to a humidifier, an air delivery conduit coupled to an outlet of the humidifier at a first end and coupled to a patient interface at the opposing end. The humidifier outlet may include a blocking member to prevent humidified gas from leaving the humidifier when there is no pressurized flow through the system.

Some embodiments relate to a method of controlling rainout in a conduit connected to a humidifier. The method may involve providing a humidifier having an outlet. The outlet may include or be adapted for coupling with a valve arrangement having a movable blocking member. The method may also involve providing a conduit adapted to couple with the outlet where the humidifier is adapted to provide a supply of humidifier gas to the conduit in use. The method may further include generating a force with a controller of a flow generator to control the movement of the blocking member, wherein in the absence of the force the blocking member is configured to obstruct the path through the outlet of the humidifier to the conduit such that no humidified gas may pass through to the conduit and subsequently rainout within the conduit, and in the presence of the force the blocking member is configured to move to unobstruct the path through the outlet of the humidifier to the conduit to allow the humidified gas to flow through to the conduit. The force may be provided by a pressurized gas flow through the humidifier to the outlet. The pressurized gas may be provided by the flow generator coupled to the humidifier.

Certain embodiments relate to a method of preventing rainout in an air delivery conduit connected to a humidifier, the humidifier including an outlet that comprises a movable blocking member, wherein in the absence of pressurized flow through the outlet the blocking member is configured to block the path through the outlet of the humidifier to the air delivery conduit and in the presence of pressurized flow the blocking member is configured to move to unblock the path through the outlet of the humidifier to the air delivery conduit to allow the pressurized flow to travel through the air delivery conduit.

Although certain embodiments have been described with respect to respiratory humidification systems it is appreciated that any humidification system or vapor transfer system may utilize such a blocking member arrangement to prevent vapor or humidified air to exit the humidification system or vapor transfer system when not in use, or there is no flow.

It is noted that there are other types of humidification systems that require the use of conduits to provide or transport the humidified gas to the desired location. Such systems are also encompassed within the scope of the present technology.

Other embodiments, aspects, features, and/or advantages of this technology will become apparent from the following detailed description when taken in conjunction with the accompanying drawings, which are a part of this disclosure and which illustrate, by way of example, principles of the disclosed technology.

BRIEF DESCRIPTION OF THE DRAWINGS

The accompanying drawings facilitate an understanding of the various embodiments disclosed. In such drawings where the same or similar numbers are used to identify similar components:

FIG. 3 schematically depicts a humidifier respiratory system connected to a nasal cannula according to an example embodiment of the technology;

DETAILED DESCRIPTION

Figure 1:
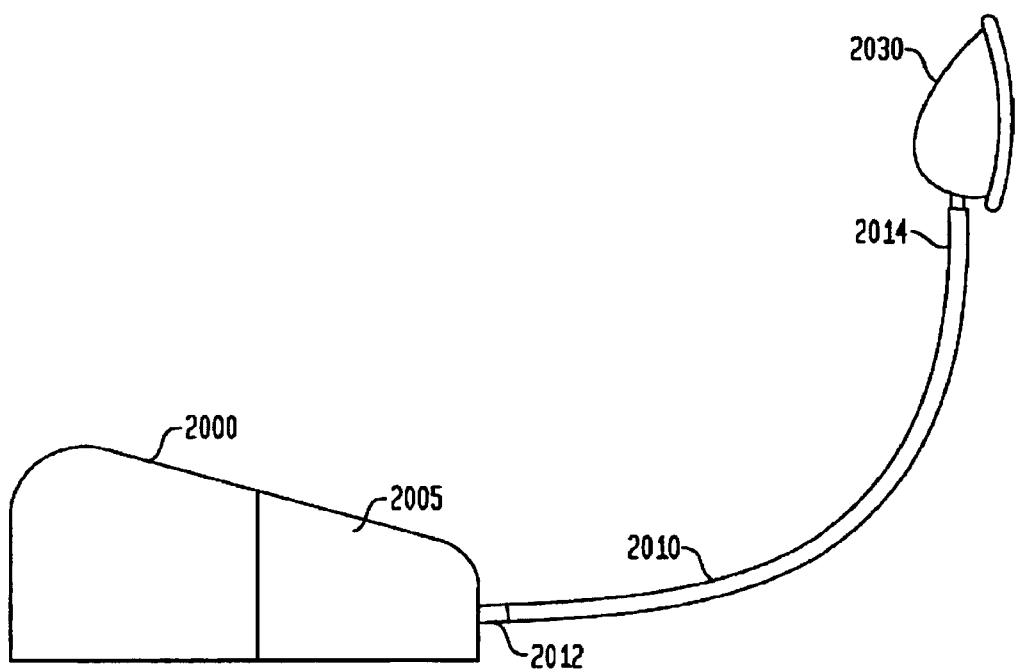
FIG. 1 schematically depicts a prior art humidifier respiratory system connected to a patient interface.
Figure 2A:
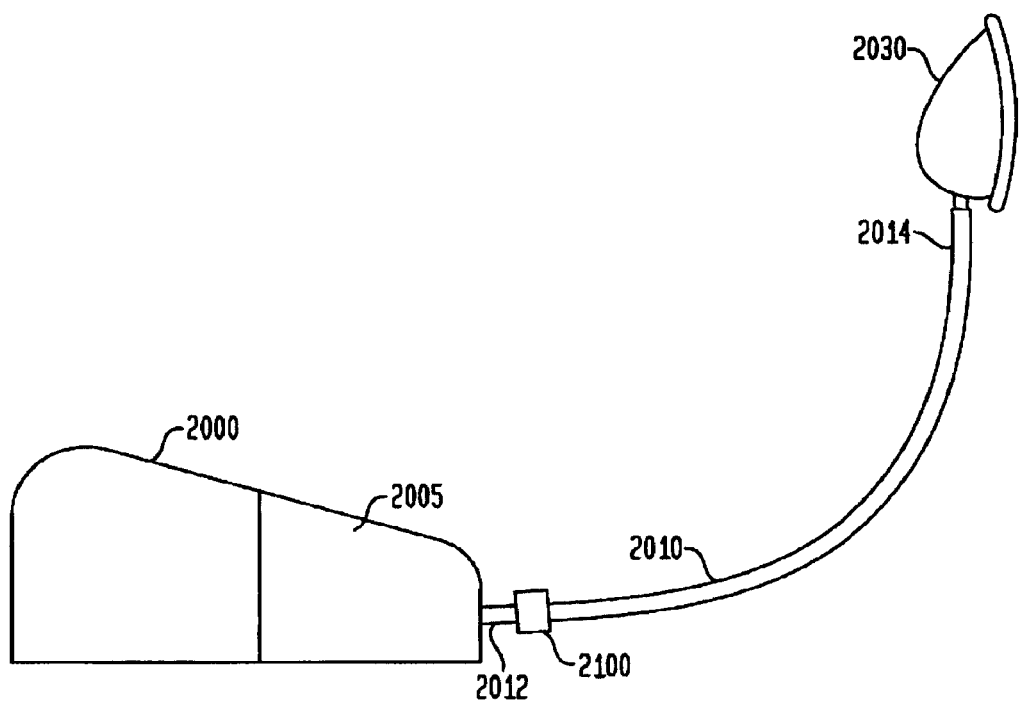
FIG. 2A schematically depicts an integrated humidifier respiratory system connected to a patient interface according to a sample embodiment of the technology.

FIG. 2A schematically depicts a certain embodiment of a respiratory treatment system. The system includes a positive airway pressure (PAP) or ventilator device 2000 attached to a humidifier 2005. In this embodiment the humidifier 2005 is integrated with the PAP or ventilator device 2000 and may optionally be removably attached. The humidifier 2005 may include any type of humidifier, including the respiratory humidifier described in co-pending International patent application publication number WO 2010/031126 filed 17 Sep. 2009. Also, any integrated PAP device and humidifier arrangements may be used, such as that described in U.S. Published Patent Application No. 2008/0072900 filed 4 May 2005, the contents of both applications are incorporated herein in their entirety.

The outlet 2012 of the humidifier is coupled to a first end of a rainout valve 2100 adapted to open and close the air path between the humidifier outlet 2012 and an air delivery conduit 2010. The second end of the rainout valve 2100 is attached to the device end of air delivery conduit 2010. The air delivery conduit 2010 is attached at the patient end to a patient interface 2030. The patient interface or mask may have any suitable configuration as is known in the art, e.g., full-face mask, nasal mask, oro-nasal mask, mouth mask, nasal prongs, etc. Also, headgear may be utilized to comfortably support the patient interface in a desired position on the patient's face.

Alternatively, the air delivery conduit 2010 may be attached to other forms of the patient interface such as a nasal cannula 2035 as shown in FIG. 3. Such a system may be used to provide respiratory therapy as described in co-owned and pending International Application Publication No. WO 2010/031126, the content of which is incorporated herein in its entirety. All other forms of patient interface such as a tracheotomy tube are also encompassed within the scope of the present technology.

Figure 2B:
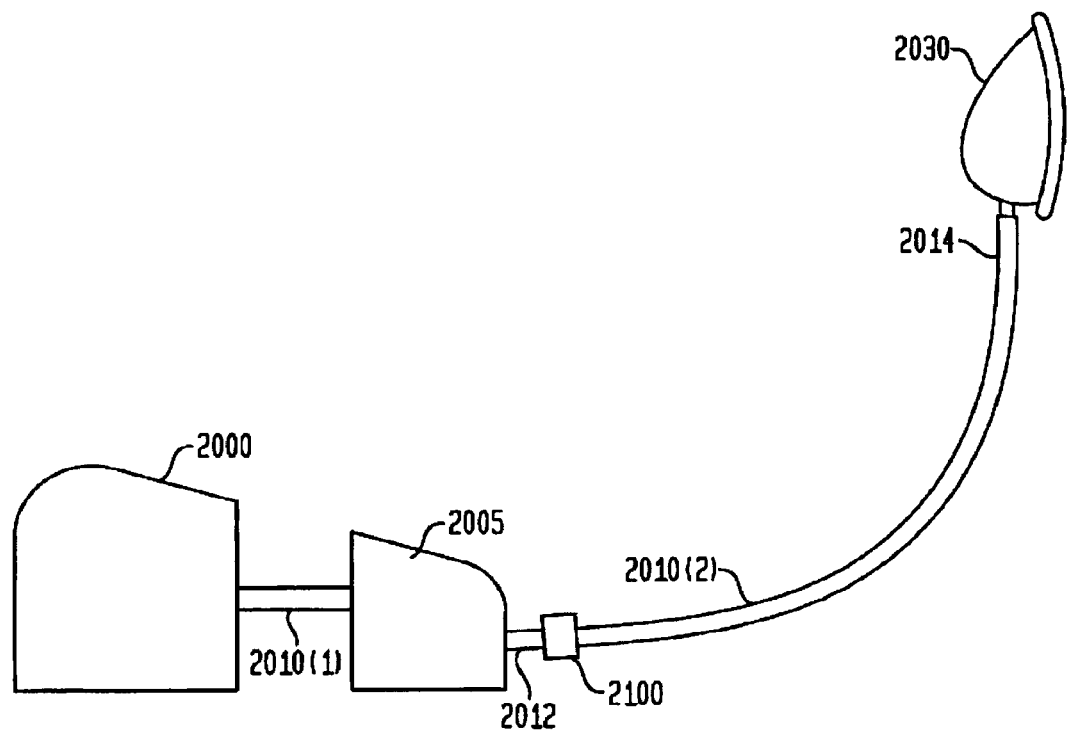
FIG. 2B schematically depicts a humidifier respiratory system connected to a patient interface according to another example embodiment of the technology.

Optionally, a further air delivery conduit may also be provided along the air delivery path. For example, as schematically shown in FIG. 2B, the humidifier 2005 may be a separate component from the PAP or ventilator device 2000 so that a first air delivery conduit 2010 (1) is placed between the PAP device 2000 and the humidifier 2005 and a second air delivery conduit 2010 (2) is placed between the rainout valve 2100 and the patient interface 2030. Optionally, an additional rainout valve 2100 (not shown) may be coupled to the inlet of the humidifier or the outlet of the PAP or ventilator device to prevent rainout or condensation from travelling back through to the PAP or ventilator device. Such a rainout valve may also prevent spillback of water into the flow generator from the humidifier.

Figure 4:
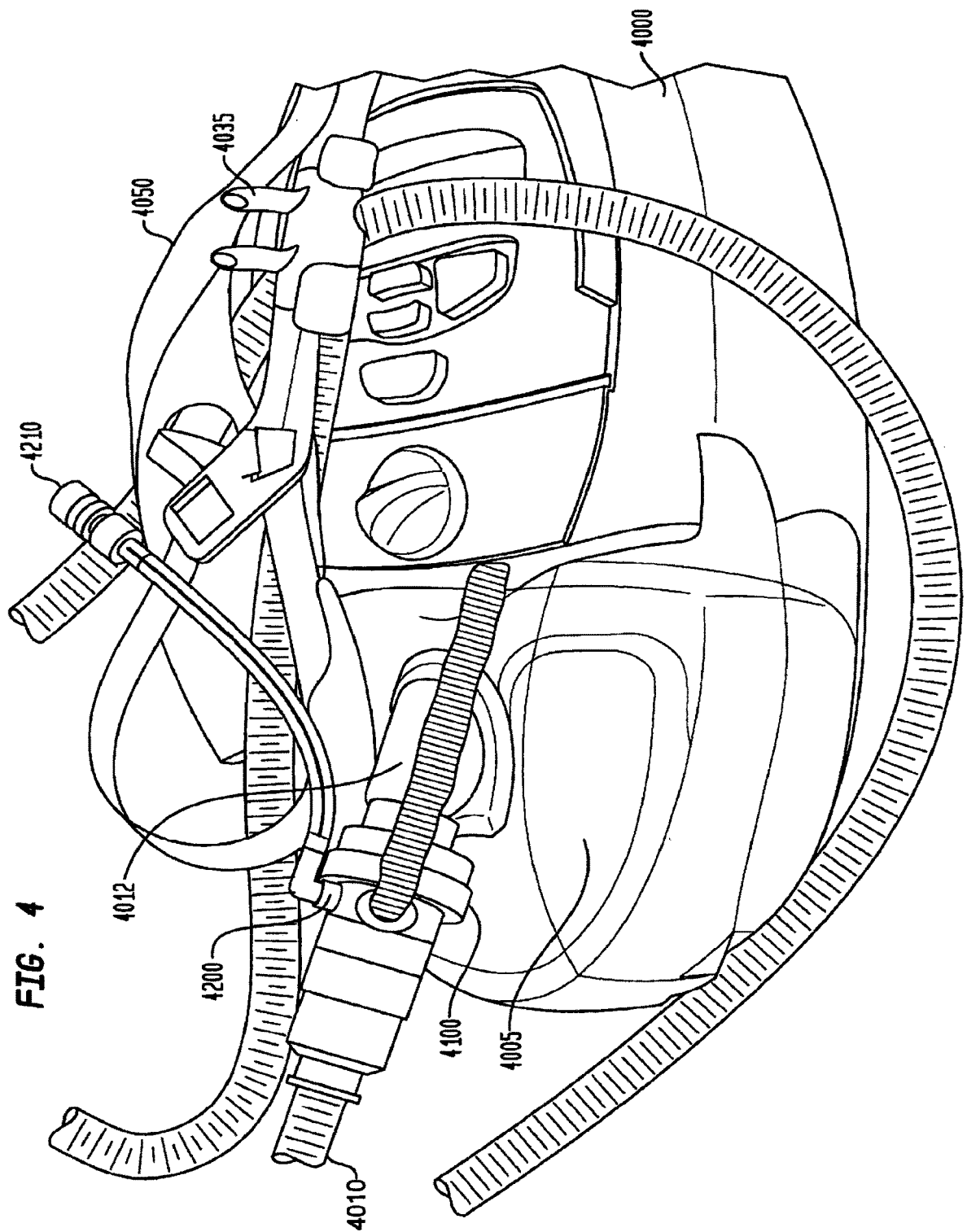
FIG. 4 is an illustration of a humidifier system according to a further example embodiment of the technology.
Figure 5:
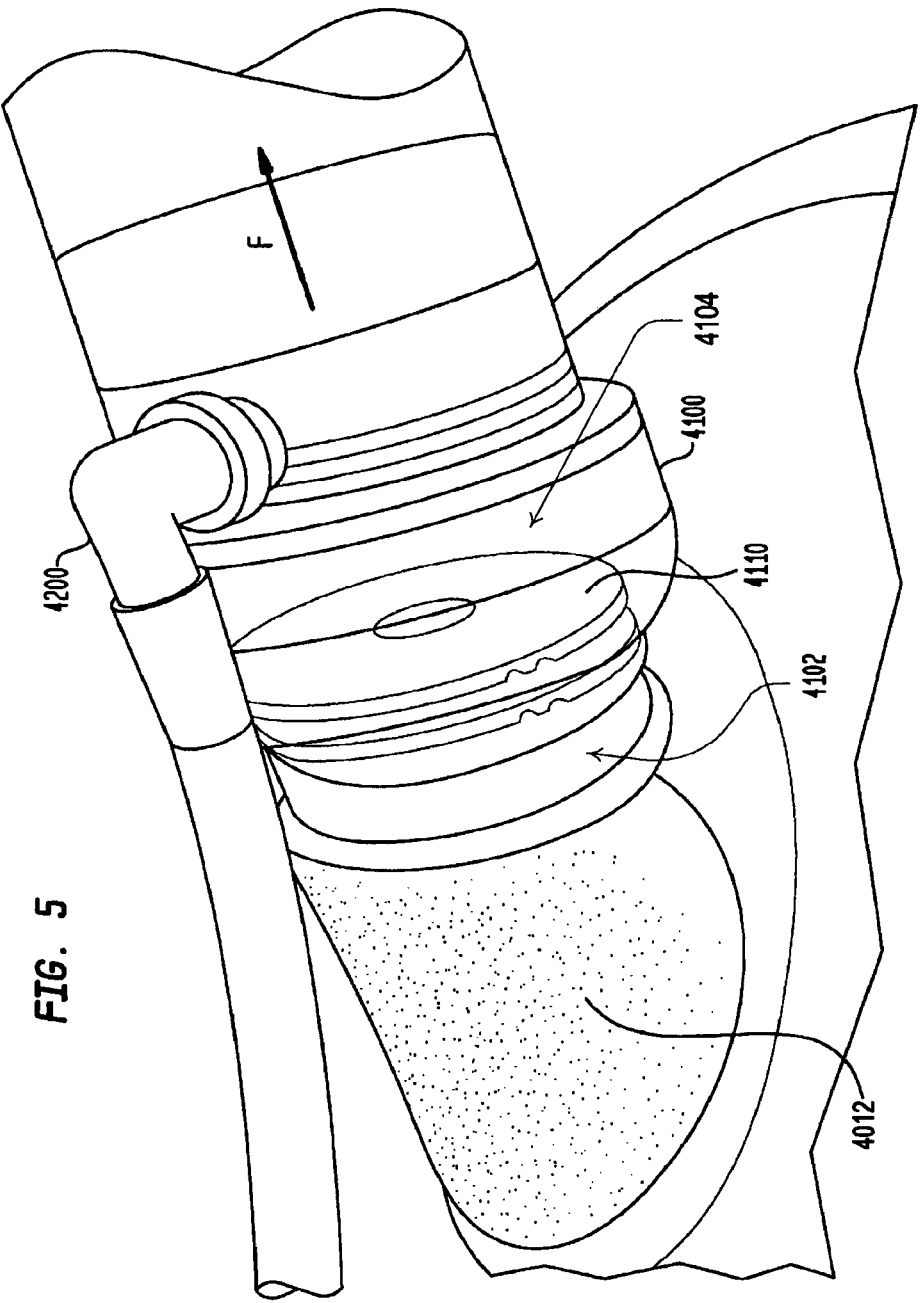
FIG. 5 is an illustration of an embodiment of the valve arrangement of the system in FIG. 4.

FIGS. 4 and 5 depict an example embodiment of a respiratory treatment system with a PAP device 4000 coupled to a humidifier 4005 including a rainout valve 4100. The humidifier 4005 may include a removable water tub for ease of filling and cleaning of the water tub as described in U.S. Published Patent Application No. 2008/0072900. The outlet 4012 of the humidifier 4005 may be attached to the rainout valve 4100. The rainout valve 4100 is coupled on the opposing end to an air delivery conduit 4010. The air delivery conduit 4010 is coupled to a nasal cannula 4035 that is attached to headgear 4050 to support the nasal cannula 4035 on a user's face.

In certain embodiments the rainout valve 4100 may include a gas port 4200 to allow an optional connection of a supplementary gas, such as oxygen to be provided to the user if desired. The supplementary gas supply may be coupled to a gas connector 4210 using a standard gas connection.

FIG. 5 is a close up view of the rainout valve 4100 of FIG. 4 attached to the humidifier outlet 4012. In this embodiment, the rainout valve 4100 includes a movable membrane 4110 within an internal channel. The membrane 4110 is adapted to move, such as by deforming, swinging and/or shifting etc., to open and close the channel to selectively block vapor through the internal channel of the rainout valve 4100 depending on the presence or absence of a pressurized flow from the flow generator. In this regard, the internal channel is configured to allow a flow of humidified gas to travel from a first side or humidifier side 4102 of the rainout valve 4100 to a second side or air delivery conduit side 4104 of the rainout valve 4100 when the flow is pressurized by the flow generator but to prevent warm vapor from moving from the first side to the second side when the flow generator is not generating its pressurized flow. Thus, in use the PAP device 4000 generates a supply of pressurized gas that is delivered to the humidifier 4005 where water vapor is added to the pressurized gas to form a humidified pressurized gas flow. The humidified pressurized gas flow travels from the humidifier 4005 to the humidifier outlet 4012 and through to the rainout valve internal channel from the first side 4102 pushing the membrane open (e.g., upwards towards the second side 4104) and then to the air delivery conduit 4010 and through to the patient interface 4035 to provide the humidified gas to the user. The direction of the gas flow generated by a flow generator of the PAP device 4000 in the system is shown by arrow F in FIG. 5. As previously mentioned, other forms of patient interface, such as a mask, nasal prongs, etc. may also be utilized.

Thus, the rainout valve 4100 membrane is adapted to serve as a vapor barrier to cover or obstruct the internal channel when there is no flow entering the rainout valve from the flow generator. For example, the membrane barrier may be configured to have a default or normally closed position to close or shut off the internal channel and prevent warm humidified air from travelling from the first side 4102 to the second side 4104 of the rainout valve 4100. This can prevent the warm humidified air from entering any conduit, such as air delivery conduit 4010 or other device attached to the second side 4104 of the rainout valve 4100 when no flow generator flow is provided, such as when the device is switched off after use or between periods of use. Warm humidified air, if allowed to enter the air delivery conduit 4010, other conduit or other device, may cool within the conduit or device and form condensate. The rainout valve 4100 prevents or at least reduces the level of condensate formed in the air delivery conduit 4010, other conduit or device.

In contrast, when the flow generator is operating to provide a pressurized flow through the rainout valve, for example, through the humidifier outlet 4012 from the humidifier 4005 and PAP or ventilator device 4000, the membrane 4110 is opened (e.g., pushed upwards towards the second side 4104 of the rainout valve 4100) by the gas flow so as to selectively open the vapor barrier. This permits the humidified pressurized gas to travel through the internal channel and around the membrane 4110 through to the second side 4104 of the rainout valve 4100.

Figure 6A:
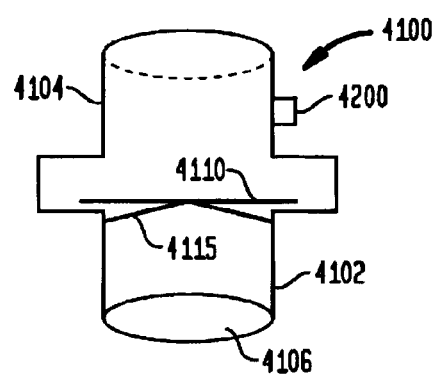
FIGS. 6A and 6B schematically depict a valve arrangement including a membrane mechanism without a flow force and with a flow force respectively according to an embodiment of the technology.
Figure 7A:
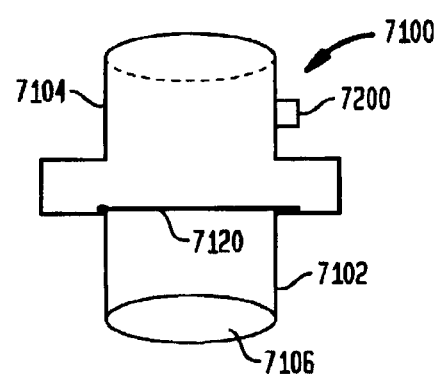
FIGS. 7A and 7B schematically depict a valve arrangement including a flap mechanism without a flow force and with a flow force respectively according to a second sample embodiment of the technology.

In such a system, the vapor barrier of the valve may also be configured to prevent the rebreathing of carbon dioxide if the expired carbon dioxide cannot travel back through the system. In this regard, the vapor barrier or blocking member may also be configured to serve as a backflow preventer to prevent any back flow from the second side to the first side (e.g., from the patient interface through to the humidifier and/or flow generator of the PAP device). For example, a higher air pressure at the second side 4104 (e.g., due to patient expiration) relative to the pressure at the first side 4102 may force or permit the membrane to close the channel (e.g., such as if the larger membrane plys against a smaller aperture structure of the channel to block the channel as illustrated in FIGS. 6A, 7A and 9A) or may permit the membrane itself to close to its normal position (such as in the case of the duckbill blocking member illustrated in FIG. 8A). This may occur even when the flow generator is operating. As a result, the flow of expired air may be prevented by the membrane from passing from the second side and entering into the humidifier 4005 and/or PAP device 4000. Thus, the expired air is prevented from travelling back to the motor or blower and can prevent contamination or deterioration of these flow generator components by thereby preventing a back flow of any humidified gas and/or any supplemental gas such as oxygen, to these components. Similarly, the back flow prevention can prevent the expired air and/or supplemental gas from entering the humidifier and potentially harming or contaminating the components of the humidifier as well. Each of the embodiments described herein may optionally be configured to serve as such a back flow preventer.

The gas port 4200 may be attached or formed at second side 4104 of the rainout valve 4100. A supplementary gas supply such as oxygen, heliox, nitrox, etc. may be attached to the gas port 4200 to supply the user with a gas, (e.g., oxygen enriched supply of pressurized gas). The supplementary gas may be provided from a pressurized source and may be continuously provided through the gas port 4200. The supplementary gas, (e.g., oxygen) travels up through the air delivery conduit 4010 and the patient interface 4035 to the user or patient. The supplementary gas will be delivered to the user or patient during inspiration. When the valve also serves as a back flow preventer as previously described, the valve may also help to reduce waste of the supplemental gas. For example, during expiration, when the user or patient is exhaling, a higher pressure may be generated by the patient's exhalation at the patient interface relative to a lower pressure at the flow generator. This difference in pressure may result in the closing of the membrane in the channel as previously described when the membrane is configured to serve as a back flow preventer. As a result, the supply of supplementary gas will build up between the rainout valve 4100 and the air delivery conduit 4010 rather than being vented back out through the humidifier and/or PAP device. Thus, the air delivery conduit 4010 accumulates a reservoir of supplementary gas that is ready to be delivered to the user or patient when inspiration commences. Advantageously, this reduces the wastage of supplementary gases during expiration as all or substantially all of the supplementary gas is supplied during inspiration. Consequently a lower level of supplementary gas may be required. It is estimated that a reduction in the supplementary gas usage, such as oxygen usage, results in approximately half the standard usage of supplementary gas or oxygen. The usage savings and improved efficiency may result in savings of more than 50% of the standard usage requirements.

In a further embodiment, the gas port 4200 may be used to provide other substances such as medications that may be required by the users. For example, asthma medications or other such medications may be applied to the gas port 4200.

Optionally, gas port 4200, or another similarly situated port, may be coupled to a humidifier bypass tubing or other conduit that is sourced from the flow generator. Such a bypass tubing may be utilized to channel a flow of dry air from the flow generator to the patient interface conduit at the second side of the rainout valve without passing through the humidifier. The flow of dry air through such a humidifier bypass channel may be generated while the rainout valve is closed and may be utilized to clear out any moist or humidified air that might remain in the patient interface conduit at the conclusion of a treatment session in a shut down procedure. This may help to further reduce rainout.

For example, for such a shut down procedure, a diverter may be activated to divert the flow generator's flow of breathable gas from traversing through the humidifier to instead traverse through the bypass tubing. This would permit the rainout valve to be closed during the shut down procedure. The diverter may be a simple manual valve or one or more flow control valves that are set by a processor or controller of the PAP device. In such a case, the processor may be configured with control instructions to control the diverter and flow generator. The processor may perform the shut down procedure by controlling switching of the diverter to the bypass channel and thereafter controlling the blower to generate the dry flow of air through the bypass channel at the completion of a treatment session for a brief period of time (e.g., 30 seconds). In some such embodiments, an electro-mechanical valve (e.g., a three port, two way valve) may serve as the diverter. However, other devices may be implemented to send the flow to the patient interface conduit from the flow generator so as to bypass the humidifier.

Figure 16:
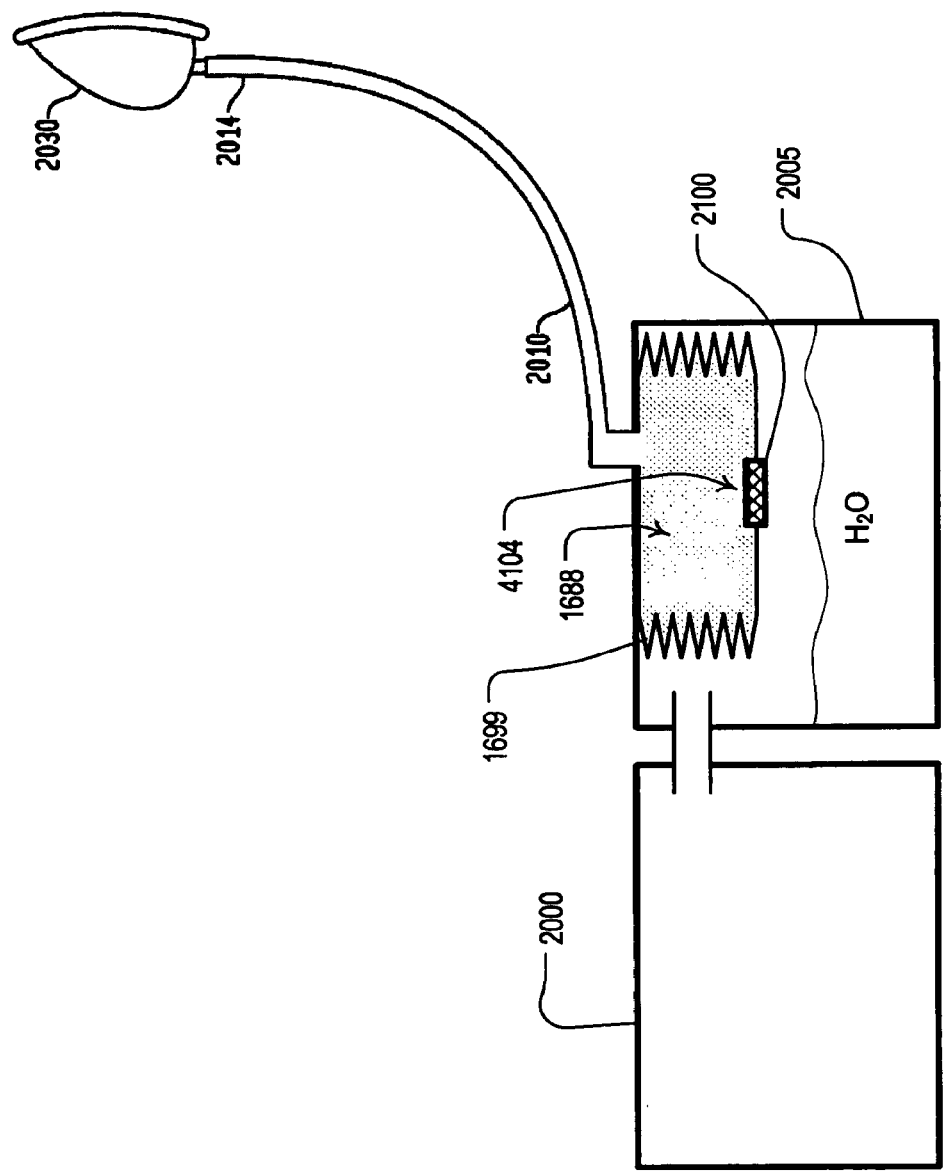
FIG. 16 illustrates a respiratory treatment system with a rainout valve arrangement having an expandable chamber that is suitable for CPAP treatment.

In a further embodiment, for constant positive airway pressure (CPAP) therapy where a constant positive airway pressure is required throughout the breathing cycle, a system to maintain the constant pressure may be required. For example, as illustrated in FIG. 16, the rainout valve 2100 may include a chamber 1688 having an expandable volume to receive the expired gas from the patient located on the patient side of the rainout valve mechanism (i.e., on the second side 4104 of the rainout valve). Such a chamber may include complaint walls 1699 that allow the expired gas to expand the chamber and prevent the closure of the valve during use, thus maintaining a constant positive pressure. Alternatively, an exhalation valve may be located proximal to the mask to prevent the pressure of the expired gas from shutting the rainout valve.

Figure 6B:
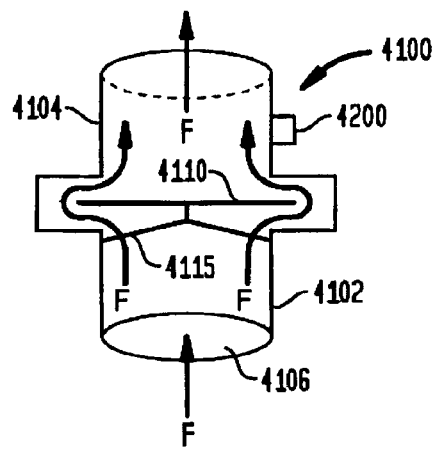

FIGS. 6A and 6B schematically illustrate a membrane type valve, which may be formed by a flexible, resilient material, as shown in the embodiment in FIGS. 4 and 5. FIG. 6A illustrates the rainout valve 4100 and membrane 4110 when there is no pressurized flow through an internal channel 4106 of the rainout valve 4100, for example flow from a humidifier. The internal channel 4106 is blocked or covered by the membrane 4110 in the relaxed or default position when there is no flow through the rainout valve. The membrane may be adapted with a shape to be generally complementary to the internal channel to block the channel. For example, it may have a slightly larger diameter than the diameter of the channel in the event of a cylindrical shaped channel. Alternatively, the membrane may have a bellows type shape such that it may balloon up to deform so as to draw in the sides when gas flow enters the bellows to allow gas flow around the bellows. Still further, other membrane shapes may be implemented for blocking the internal channel when there is no flow from the flow generator. The membrane 4110 is generally configured to cover or block the internal channel 4106 to selectively prevent vapors or humidified gas to pass from the first side 4102 to the second side 4104 under certain conditions. The membrane 4110 may be supported within the internal channel 4106 via a support structure 4115. As described above a supplementary gas port 4200 may optionally be attached to the second side 4104 of the rainout valve.

FIG. 6B illustrates the rainout valve 4100 and membrane of FIG. 6A when there is pressurized flow through the internal channel 4106 of the rainout valve (e.g., a higher gas pressure at the first side relative to the gas pressure of the second side). The pressurized gas flow F enters the internal channel 4106 from the first side 4102 and pushes the membrane to allow the gas to flow around the membrane and through to the second side 4104. The membrane 4110 configured to move or deform at a desired level of flow (e.g., a flow between 4 to 120 L/min). However, the membrane may be implemented to move with other flow rates and may move proportionally depended upon the level of flow provided. The membrane 4110 remains open while there is pressurized flow through the internal channel 4106. When the pressurized flow stops or is turned off the membrane 4110 will return to the default or relaxed position and block the internal channel 4106 as illustrated in FIG. 6A.

The above valve arrangements have been described using a membrane type vapor barrier. However, other types of valve systems utilizing other forms of blocking means or vapor barriers may also be implemented to selectively block the internal channel of the rainout valve. Some additional example embodiments of the rainout valve are illustrated in FIGS. 7A to 10B and are described in more detail herein.

Figure 7B:
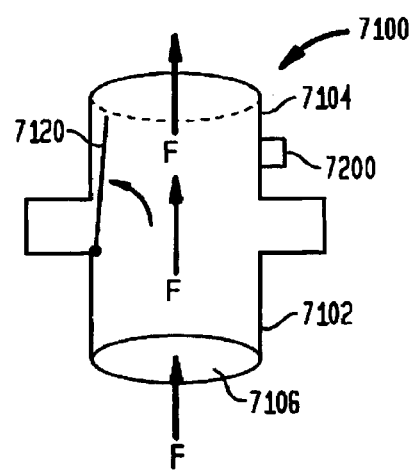

FIGS. 7A and 7B schematically illustrate another example embodiment of a rainout valve 7100 where the blocking member is a flap, such as a hinged flap or a resilient silicone flap, that is configured to close and open access through the internal channel 7106 of the rainout valve 7100. FIG. 7A illustrates the position of the flap 7120 when there is no flow through the system and the flap is in the relaxed or default position. The flap 7120 is configured to have a complementary shape to the internal channel with a slightly larger size (e.g., diameter). In this position the flap 7120 selectively prevents the transport of vapor or humidified gas from flowing through to the second side 7104 of the rainout valve.

FIG. 7B illustrates the action of the flap 7120 when there is pressurized gas flow F through the internal channel 7106. The pressurized gas flow forces the flap to deform and/or swing to open the internal channel from the first side 7102 to the second side 7104. The flap 7120 remains open while there is pressurized flow through the internal channel 7106. When the pressurized flow stops (e.g., if the flow generator is turned off, if there is an equal gas pressure in the channel on either side of the flap and/or if a higher gas pressure exists in the channel on the second side relative to the channel gas pressure of the first side, the flap 7120 will return to the default position and block the internal channel 7106 (i.e., the normally closed position). The rainout valve 7100 may optionally include a supplementary gas port 7200 on the second side 7104 of the rainout valve adapted to receive a supply of supplementary gas.

Figure 8A:
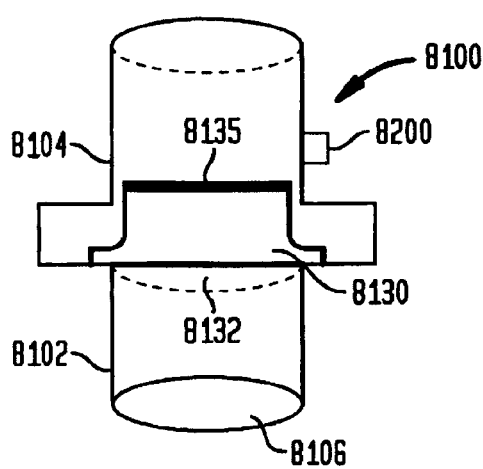
FIGS. 8A and 8B schematically depict a valve arrangement including a duckbill mechanism without a flow force present and with a flow force present respectively according to a third example embodiment of the technology.
Figure 8B:
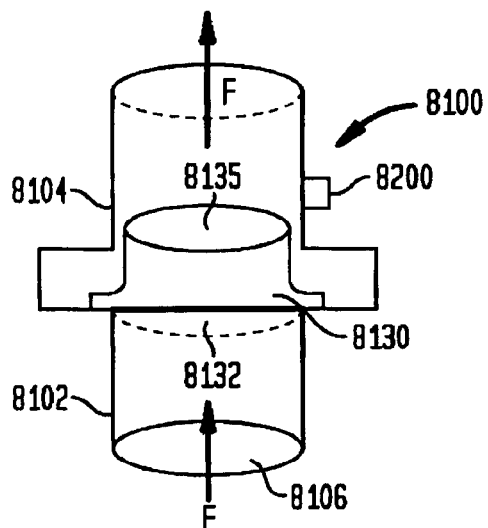
Figure 9A:
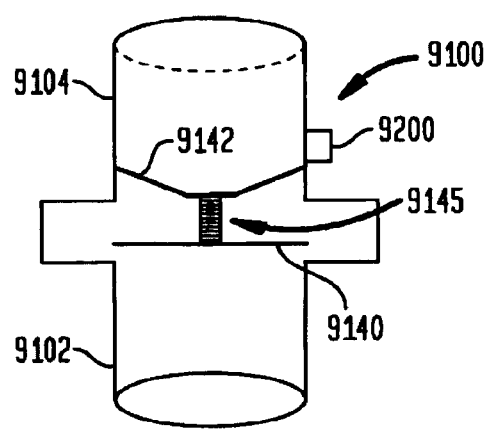
FIGS. 9A and 9B schematically depict a valve arrangement including a spring mechanism without and with the presence of a flow force respectively according to a fourth sample embodiment of the technology.

FIGS. 8A and 8B schematically illustrate another example embodiment of a rainout valve 8100 where the blocking member or vapor barrier has a duckbill arrangement 8130. FIG. 8A illustrates the duckbill arrangement 8130 when there is no flow through the system and the duckbill arrangement 8130 is in the relaxed or default position. In the relaxed or normally closed position the duckbill arrangement 8130 has a duck beak like end 8135 such that two sides of the beak type end 8135 are resiliently and coextensively aligned together to form a seal or vapor barrier to prevent the transport of vapor or humidified gas from the first side 8102 through to the second side 8104 of the rainout valve 8100. The opposing end 8132 of the duckbill arrangement 8130 has a generally tubular or cylindrical opening. The opposing end 8132 may optionally be inserted over an end of a tube outlet such as a humidifier outlet and no further valve housing structure maybe required (not shown). The duckbill valve may be manufactured from an elastomeric material such as rubber.

FIG. 8B illustrates the action of the duckbill arrangement 8130 when the flow generator generates the pressurized gas flow F through the opposing end 8132 to the beak type end 8135 of the duckbill arrangement 8130. The pressurized gas flow forces the two sides of the beak type end 8135 to deform outwards to open the duck beak and then enters the internal channel from the first side 8102 to the second side 8104. The duckbill arrangement 8130 remains open while there is pressurized flow through the internal channel 8106. When this pressurized flow stops (e.g., the flow generator is turned off), the two sides of the beak type end 8135 will return to the default position and block the internal channel 8106. The rainout valve 8100 may optionally include a supplementary gas port 8200 on the second side 8104 of the rainout valve adapted to receive a supply of supplementary gas.

Figure 9B:
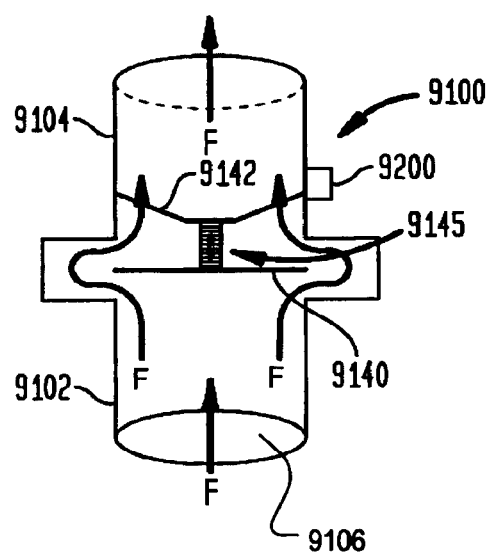

FIGS. 9A and 9B schematically illustrate another example embodiment of a rainout valve 9100 where the vapor barrier or blocking member 9140 is controlled by a biasing member such as a spring 9145. The spring may be attached or incorporated with the blocking member 9140 and a support structure 9142 fixed within the internal channel 9106. The blocking member 9140 may be made from any lightweight material, such as a thin plastic disc, and is adapted to block or close off access through the internal channel 9106 of the rainout valve 9100 when there is no pressurized flow therethrough. The blocking member 9140 may be configured to have a complementary shape to the internal channel (e.g., with a slightly larger diameter). However, it is appreciated that other blocking member shapes may be used. FIG. 9A illustrates the biasing member providing a biasing force to normally close the vapor barrier of the valve. For example, the spring 9145 in a relaxed or relatively uncompressed state maintains the blocking member in a sealed position when there is no flow through the system. Under this condition, the blocking member 9140 is selectively located in a position to seal or block the internal channel 9106. Thus, the blocking member 9140 may also be in a relaxed or default position. In this position the blocking member 9140 prevents the transport or vapor or humidified gas from flowing through from the first side 9102 to the second side 9104 of the rainout valve 9100.

FIG. 9B illustrates the action of the biasing member such as the spring 9145 and blocking member 9140 when there is pressurized gas flow F through the internal channel 9106. The pressurized gas flow pushes the blocking member 9140 to shift the blocking member (e.g., upwards) and compresses the spring 9145 to open the internal channel from the first side 9102 to the second side 9104 allowing the pressurized gas to flow through the internal channel 9106. The blocking member 9140 remains open with the spring 9145 compressed while there is pressurized flow through the internal channel 9106. When the pressurized flow stops or is turned off the blocking member 9140 is no longer forced upwards and the spring 9145 returns the blocking member 9140 to the normally closed position to block the internal channel 9106. The rainout valve 9100 may optionally include a supplementary gas port 9200 on the second side 9104 of the rainout valve adapted to receive a supply of supplementary gas.

Although the resilient biasing member in this embodiment is configured to compress as a result of a flow from the flow generator, in an alternative embodiment, the biasing member may be configured on the opposite side of the blocking member from that illustrated in FIGS. 9A and 9B such that movement of the blocking member as a result of the flow stretches the resilient biasing member. In the absence of flow the biasing member is configured to recoil or contract to its normal or default position to block the passage from the first side 9102 to the second side 9104. Thus the biasing force from the recoiling or contracting applied to the blocking member will then move the blocking member to again seal the channel to reduce vapor transfer through the channel.

Figure 10A:
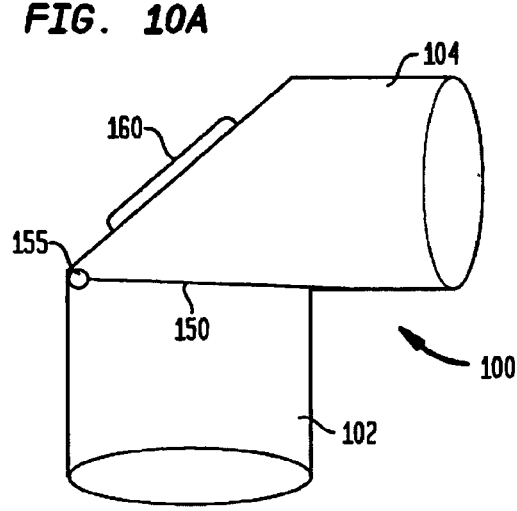
FIGS. 10A and 10B schematically depict a valve arrangement further including a vent to atmosphere without and with the presence of a flow force respectively according to a further sample embodiment of the technology.
Figure 10B:
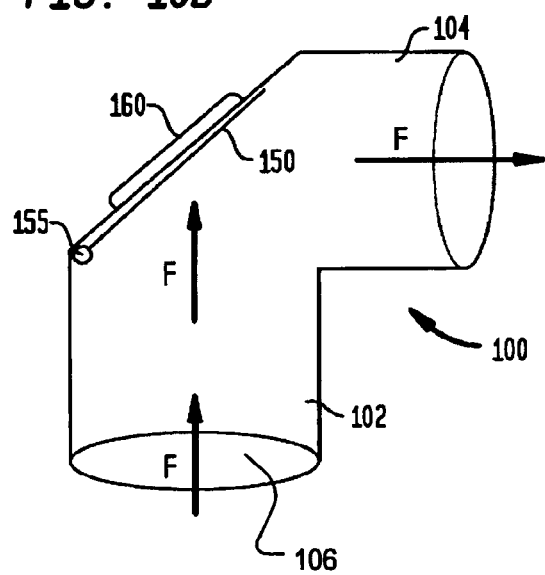

FIGS. 10A and 10B schematically illustrate another example embodiment of a rainout valve 100 having a blocking member 150, such as one or more flaps or hinged flaps. In this embodiment the rainout valve 100 includes an internal channel 106 to transport the supply of pressurized gas from a first side 102 to a second side 104. The blocking member or flap is adapted to block the passage through the internal channel 106 from the first side 102 to the second side 104 in the default (normal) or relaxed position as shown in FIG. 10A. An aperture 160 to atmosphere is provided on a surface on the second side 104 of the rainout valve 100. The flap is attached or hinged at a junction 155 between the aperture 160 and the blocking region of the internal channel 106. The flap is adapted to pivot and/or flex to move between a first position and a second position. The first position may be a default or relaxed position when there is no pressurized flow through the internal channel from the flow generator. In this first default or relaxed position the flap blocks the access through the internal channel 106 from the first side. However, the aperture 160 is open to atmosphere as shown in FIG. 10A for access to the channel at the second side. Having the second side 104 of the rainout valve open to atmosphere in this way allows any humidified gas present in the second side 104 or in the air delivery conduit or device attached to the second end 104 of the rainout valve to be vented to atmosphere. This may allow the second side 104 that is attached to the air delivery conduit or patient interface to dry. This is particularly useful after a treatment session with the respiratory treatment apparatus when a supply of humidified gas has been provided through the system. The remaining warm moist gas may escape through the aperture 160 to atmosphere rather than being trapped and allowed to condense within the attached air delivery conduit or other attached device.

In contrast, as seen in FIG. 10B, when the flap is forced or pivoted to the second position, such as by the pressurized gas flow F, to unblock or open the internal channel 106 from the first side 102 to the second side 104, and to substantially simultaneously close or block the aperture 160 and prevent the escape of pressurized gas to atmosphere through the aperture 160. In this way, the blocking member or vapor barrier is operable to selectively permit or prevent vapor from entering the channel from the first end that may be associated with a humidifier output, and to selectively permit or prevent vapor from exiting the channel to atmosphere.

In these embodiments, the blocking member 150 is illustrated as a flap but may be implemented by any other form of valve arrangement. Optionally in another embodiment the aperture 160 may be adapted to be removably plugged with an adaptor configured to allow the connection of a supplementary gas supply when required instead of being used as an aperture to atmosphere in a similar manner to the embodiments described above. It may be desirable to block the vent to atmosphere when using a supplementary gas source as this may result in wastage of the supplementary gas.

Figure 11:
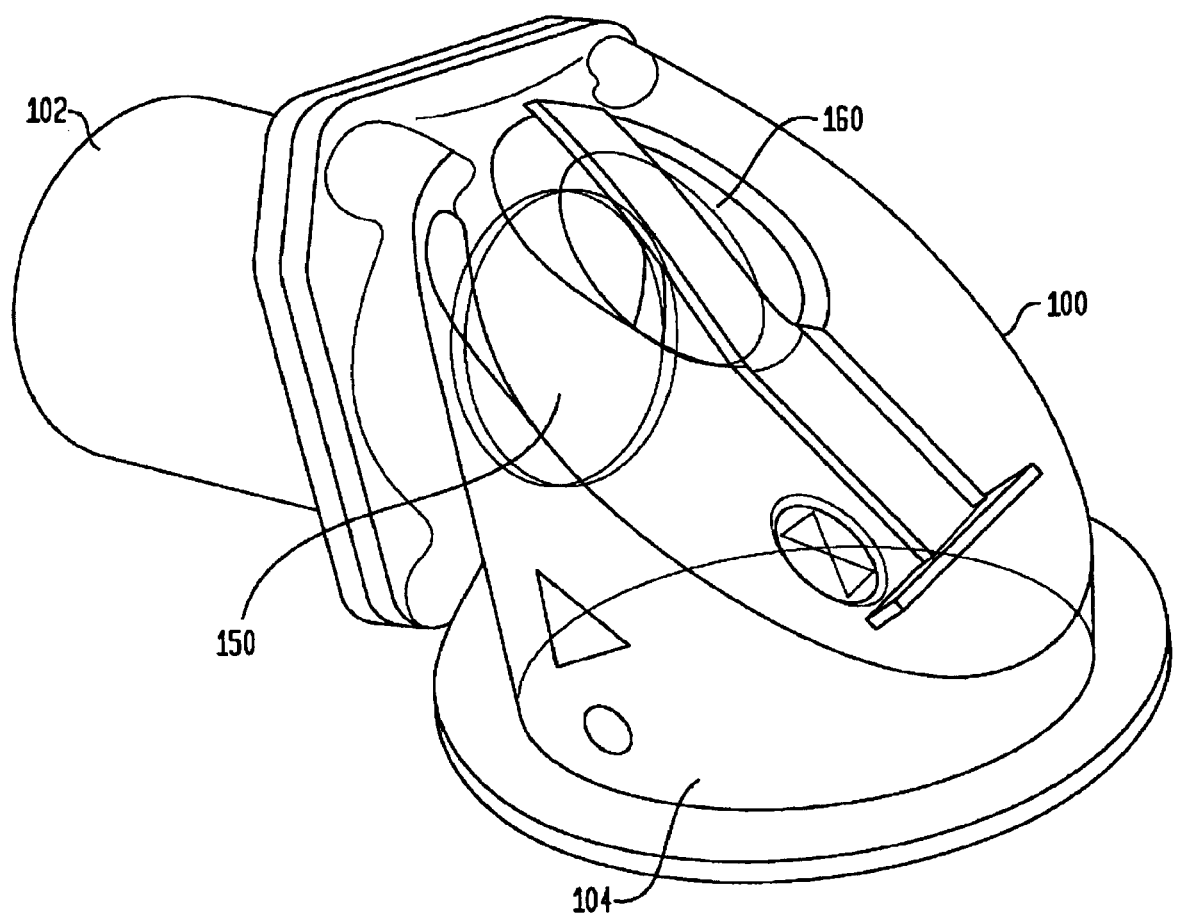
FIG. 11 is an illustration of the outside of a valve arrangement further including a vent to atmosphere showing the arrangement when there is no flow through the valve from the flow generator.
Figure 12:
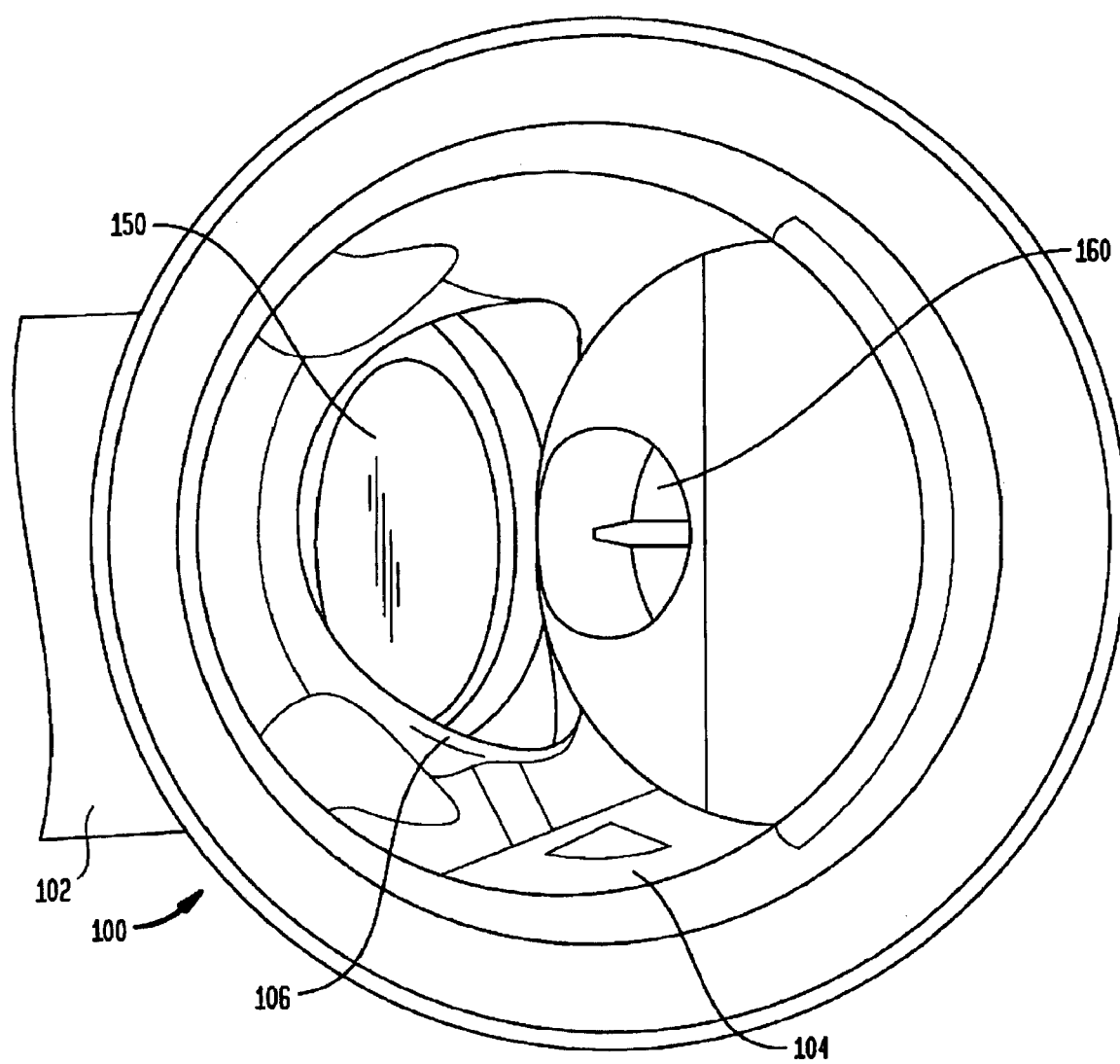
FIG. 12 is an illustration of the inside view of the valve arrangement of FIG. 11 when there is no flow in the channel of the valve from the flow generator.

FIGS. 11 to 14 are illustrations of a further example embodiment of a rainout valve including a vent or aperture to atmosphere similar to that described in relation to FIGS. 10A and 10B. FIGS. 11 and 12 show a blocking member 150 or vapor barrier in a relaxed or default (normal) position from an outside view and inside view respectively. In this version, the vapor barrier may be formed by a flap that is operable to selectively block the internal channel between the first side 102 and the second side 104. The aperture 160 is shown open to atmosphere.

Figure 13:
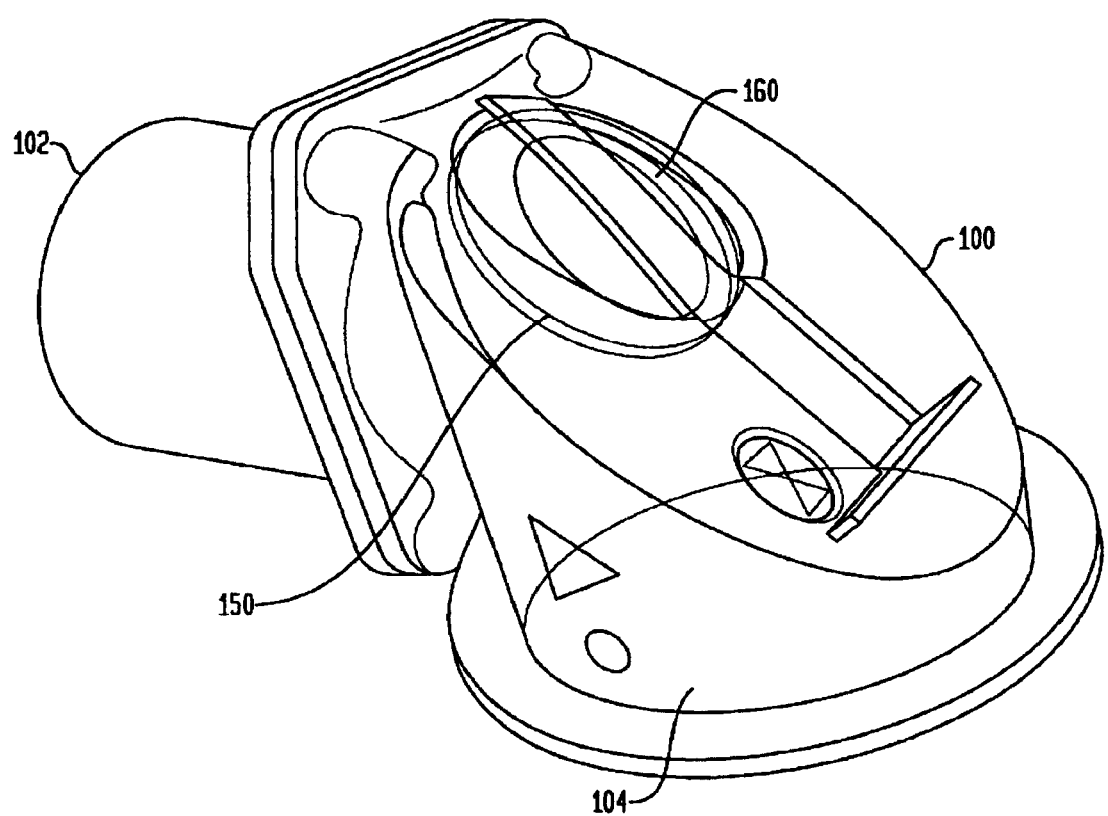
FIG. 13 is an illustration of the outside of the valve arrangement in FIG. 11 showing the arrangement when there is flow through the valve from the flow generator.
Figure 14:
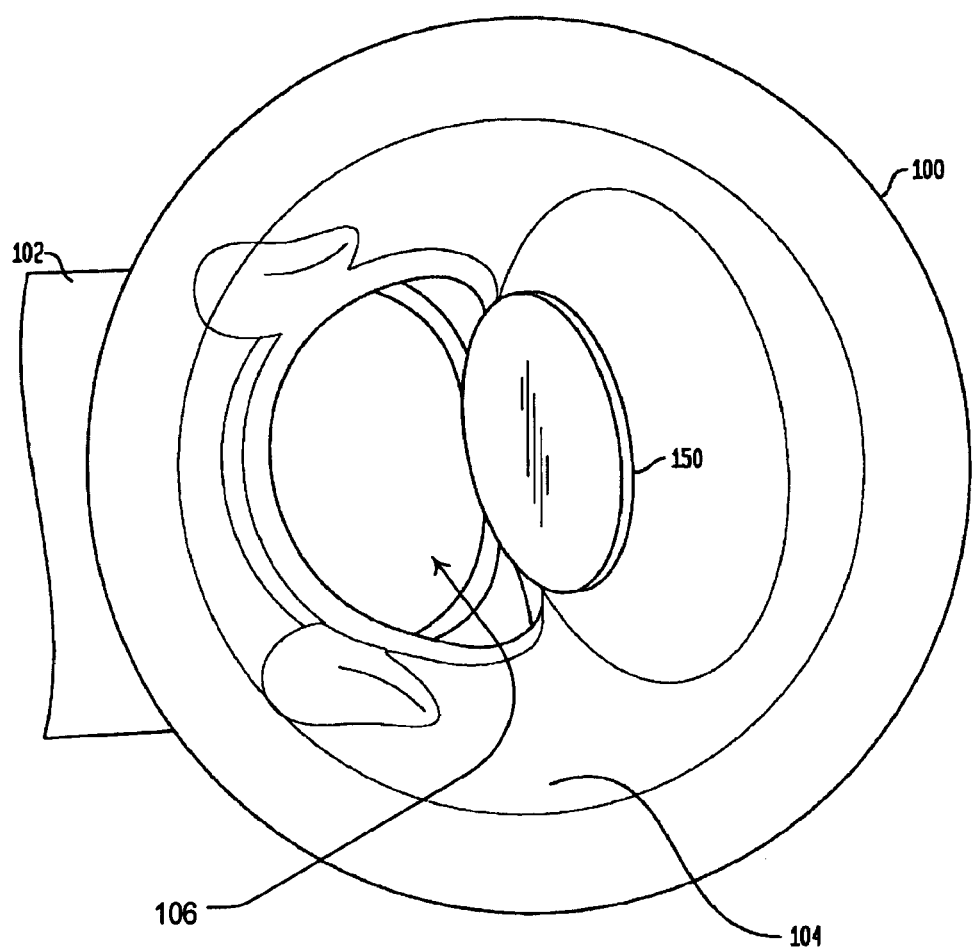
FIG. 14 is an illustration of the inside view of the valve arrangement of FIG. 13 when there is flow through the valve from the flow generator.

FIGS. 13 and 14 show the position of the flap when a force is supplied by the pressurized gas flow in the internal channel 106 and to the flap from an outside view and inside view respectively. The flap is opened within the internal channel 106 to provide access therethrough from the first side 102 to the second side 104. The flap is forced to cover or block the aperture 160 and consequently block any venting to atmosphere through the aperture 160.

Figure 15:
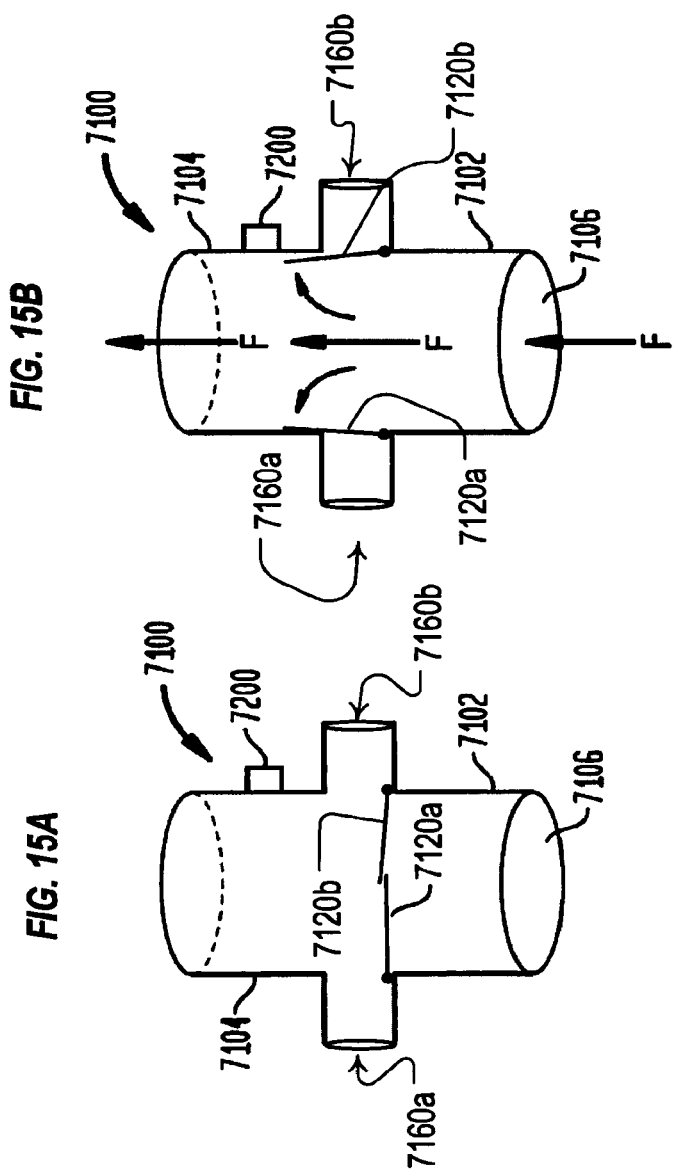
FIGS. 15A and 15B schematically depict a valve arrangement including a plurality of flaps without a flow force and with a flow force respectively according to a further example embodiment.

FIGS. 15a and 15b show a further embodiment based on a similar arrangement to that shown in FIGS. 7A and 7B but with a plurality of hinged flaps, such as two hinged flaps. In such an arrangement each flap is moved to block one or more apertures 7160a, 7160b that vent to atmosphere when a force or pressure is applied by the gas flow through the aperture from the first side 7102 to the second side 7104. One or more apertures 7160a, 7160b to atmosphere are located in the extended arms of the valve 7100.

FIG. 15A illustrates the position of the flaps 7120a, 7120b when there is no flow through the system and the flaps are in the relaxed or default positions. The flaps 7120a, 7120b are configured to overlap to obstruct the internal channel. In this position the flaps 7120a, 7120b selectively prevent the transport of vapor or humidified gas from flowing through to the second side 7104 of the rainout valve. In this arrangement one or more apertures 7160a, 7160b that vent to atmosphere are unobstructed to allow air from atmosphere to pass into the second side of the 7104 of the rainout valve. In a similar manner to that described in relation to FIG. 10a above.

FIG. 15B illustrates the action of the flaps 7120a, 7120b when there is pressurized gas flow F through the internal channel 7106. The pressurized gas flow forces the flaps to deform and/or swing to open the internal channel from the first side 7102 to the second side 7104 and simultaneously block or obstruct the one or more apertures 7160a, 7160b that vent to atmosphere to prevent gas from exiting via these apertures 7160a, 7160b. The flaps 7120a and 7120b continue to provide an open internal channel 7106 and blocked apertures 7160a, 7160b to atmosphere while there is pressurized flow through the internal channel from the flow generator. When the pressurized flow stops (e.g., if the flow generator is turned off, if there is an equal gas pressure in the channel on either side of the flap and/or if a higher gas pressure exists in the channel on the second side relative to the channel gas pressure of the first side, the flaps 7120a, 7120b will return to their default positions and block the internal channel 7106 and open the apertures 7160a, 7160b to atmosphere (i.e., the normally closed position).

It is noted that other arrangements may be utilized that move an obstruction component from a first position to a second position based on the absence or presence of pressurized gas flow through the rainout valve. Wherein in the first position the obstruction component is configured to block the passage from a first side of the rainout valve to a second side of the rainout valve while allowing venting to atmosphere. In the second position the obstruction component is configured to block the venting to atmosphere while allowing the passage of flow from a first side of the rainout valve to a second side of the rainout valve. Such mechanisms are encompassed within the scope of the present technology.

The blocking members illustrated in FIGS. 6A to 10B, 15A and 15B are shown as being located in a substantially central location of the rainout valve internal channels. However, it is appreciated that the blocking members may be located anywhere within the internal channel to block the transport of vapor or humidified gas flow from exiting the second side of the rainout valve.

In the above embodiments the rainout valve 100, 2100, 4100, 7100, 8100, 9100 is illustrated as an separate component connectable with and between the humidifier outlet 2012 and the air delivery conduit 2010, 2010 (2), for example, by a coupling or other connector. In this way, the valve may be used with many different types of respiratory treatment apparatus. However, it should also be appreciated that the rainout valve may be an integrated component of the outlet 2012 of the humidifier 2005. Alternatively, the rainout valve may be integrated into the device end of the air delivery tube 2010, 2010 (2).

The rainout valves as described above are passive pneumatically controlled rainout valves. However, it is to be appreciated that actively controlled valves such as electrically controlled, piezo-controlled, electromagnetic controlled or other such actively controlled valves may also be utilized. For example the active electromagnetically controlled valve described in International patent application PCT/AU2010/000708 filed 9 Jun. 2010, the contents of which is incorporated herein in its entirety, may be used. This active valve may be used to control the flow of warm humidified air through a humidifier system as described in the application.

Furthermore, any form of blocking means or vapor barrier configured to selectively shut off or block the transfer path from the outlet of a humidifier is encompassed within the scope of the present technology. For example, shutter systems may be employed. Furthermore, the blocking means, such as when integrated into a humidifier outlet or into an delivery conduit, may be designed in a manner to allow humidified gas to flow through the blocking means or valve during pressurized flow generation but to prevent water from spilling into the conduit. This advantageously would also prevent users from filling humidifier tube via the deliver conduit and consequently reduce the risk of overfilling the humidifier water tub.

In some embodiments, the vapor barrier may be configured so as not to prevent pressure detection across the medium of the closed barrier. Rather, it may be configured to permit a detection of pressure changes from one side of the vapor barrier that exist on the opposing side of the vapor barrier. Thus, the vapor barrier may effectively transmit the pressure changes through its medium such as by vibrating or by its pliability while it remains in a closed, vapor blocking position. For example, while the vapor barrier is closed, its pliability may allow it to expand/compress or otherwise respond to pressure changes at the patient interface side of the vapor barrier. In the case of an increase in pressure in the patient interface that may be attributable to patient expiration on the second side of the membrane, the increase in pressure may cause the membrane to expand into an area associated with the first side of the membrane (e.g., towards the flow generator and humidifier) while still preventing back flow through the rainout valve. This expansion of the vapor barrier may effectively compress the air on the first side of the vapor barrier proportionally to the compression of air on the second side of the vapor barrier. A pressure sensor located in the flow generator and/or humidifier may then be able to detect this change in pressure on the first side of the vapor barrier. Similarly, a subsequent decrease in pressure at the patient interface end (e.g., patient inhalation) may permit the membrane of the vapor barrier to relax (even before it opens) so as to reduce the pressure at the first side of the vapor barrier proportionally to the reduction on the second side proximate to the patient interface.

Accordingly, even when the vapor barrier acts as a back flow preventer, it may be configured to allow sensing of pressure changes attributable to the patient interface side without using a pressure sensor at the patient interface side. That is, a pressure sensor may still be implemented by the PAP device at the flow generator or humidifier side of the vapor barrier and effectively detect pressure changes through the closed barrier. This may be useful for different control routines that may be implemented by a processor or controller of the PAP device that are based on pressure detection. For example, the processor may detect an increase in pressure through the vapor barrier as a trigger for starting the flow generator as part of a SmartStart feature. Such a SmartStart procedure is described in U.S. Pat. No. 6,240,921, the disclosure of which is incorporated herein by reference. Similarly, the processor may detect a reflected oscillating pressure waveform (e.g., 4 Hz) originally generated by the flow generator that is reflected back from the patient such that it vibrates the closed vapor barrier at a velocity proportional to the reflected pressure waveform. This process may allow the controller to thereby detect an open patient airway through the closed vapor barrier. Such an open airway detection process is described in U.S. Pat. No. 5,704,345, the disclosure of which is incorporated herein by reference.

In the foregoing description and in the accompanying drawings, specific terminology, values and drawing symbols are set forth to provide a thorough understanding of the present technology. In some instances, the terminology and symbols may imply specific details that are not required to practice the technology. For example, although the terms "first" and "second" have been used, unless otherwise specified, they are not intended to indicate any order but may be utilized to distinguish between distinct elements of the technology.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise," "comprised" and "comprises" where they appear. It is further to be understood that the word "humidifier outlet" in this specification refers to any outlet from a humidifier including a water tub outlet or to an outlet to which a conduit is attached.

It will further be understood that any reference herein to known prior art does not, unless the contrary indication appears, constitute an admission that such prior art is commonly known by those skilled in the art to which the present technology relates.

Although the technology has been herein shown and described in relation to humidified respiratory apparatuses and systems it is to be understood that any humidifier system or vapor generation system may utilize such a rainout valve arrangement. The rainout valve arrangement may be coupled or attached between any such humidifier or vapor generation system and a conduit or other device in which the presence of condensate or rainout in the conduit or other device would be undesirable. Furthermore, while the humidifier respiratory system described are what is conceived to be the most practical and preferred embodiments, it is recognized that departures can be made within the scope of the technology, which is not to be limited to the details described herein but is to embrace any and all equivalent assemblies, devices and apparatus.

The invention claimed is:

1. A device to reduce conduit rainout, the device comprising:
a gas conduit having an input aperture and an output aperture, the gas conduit configured as a channel for movement of a breathable gas between the input aperture and the output aperture, wherein the gas conduit is configured to provide the breathable gas from the output aperture to a patient interface;
a pressure responsive vapor barrier operable to selectively prevent vapor passing from the patient interface through the gas conduit to the input aperture; and
a bypass conduit configured to channel a flow of dry air from a flow generator of a respiratory treatment apparatus to the gas conduit at a patient interface side of the vapor barrier when the vapor barrier selectively prevents vapor passing from the patient interface through the gas conduit to the input aperture.

2. The device of claim 1, wherein the vapor barrier is configured to normally seal the channel to prevent vapor passing from the output aperture to the input aperture.

3. The device of claim 2, wherein the vapor barrier is configured to open to permit the breathable gas to pass from the input aperture to the output aperture by an application of pneumatic pressure applied at the input aperture that exceeds the pressure at the output aperture.

4. The device of claim 3, wherein the vapor barrier is configured to close to prevent vapor passing from the output aperture to the input aperture with a pneumatic pressure applied at the output aperture that exceeds or is equal to pressure at the input aperture.

5. The device of claim 4, wherein the vapor barrier comprises a valve flap.

6. The device of claim 5, wherein the valve flap is formed of a flexibly resilient material.

7. The device of claim 4, wherein the vapor barrier comprises an aperture cover and biasing member.

8. The device of claim 1, wherein the gas conduit is configured at the output aperture as a coupling for the patient interface.

9. The device of claim 1, further comprising:
a positive airway pressure device; and
a humidifier, wherein the humidifier is coupled to the positive airway pressure device and the input aperture of the gas conduit.

10. The device of claim 1, wherein the device is an attachment at an outlet of a humidifier.

11. The device of claim 1, wherein the vapor barrier is configured for a detection of pressure changes from one side of the vapor barrier that exist on an opposing side of the vapor barrier when the vapor barrier is closed to prevent vapor passing from the output aperture to the input aperture.

12. The device of claim 1, wherein the gas conduit further comprises an atmosphere access port.

13. The device of claim 12 wherein the vapor barrier is further configured to cover the atmosphere access port when the vapor barrier permits the breathable gas to pass from the input aperture to the output aperture.

14. The device of claim 12, wherein the vapor barrier is further configured to uncover the atmosphere access port when the vapor barrier prevents vapor passing from the output aperture to the input aperture.

15. The device of claim 12, wherein the gas conduit is configured at the output aperture as a coupling for the patient interface.

16. The device of claim 12, wherein the vapor barrier comprises a bellows.

17. The device of claim 12, wherein the vapor barrier comprises a duckbill valve.

18. The device of claim 12, wherein the gas conduit is configured at the input aperture as a coupling for a humidifier.

19. A device to reduce conduit rainout, the device comprising:
a gas conduit having an input aperture and an output aperture, the gas conduit configured as a channel for movement of a breathable gas between the input aperture and the output aperture, wherein the gas conduit is configured to provide the breathable gas from the output aperture to a patient interface;
a vapor barrier operable to selectively prevent vapor passing from the patient interface through the gas conduit to the input aperture;
a pressure sensor located upstream of the vapor barrier;
wherein the vapor barrier is configured to normally seal the channel to prevent vapor passing from the output aperture to the input aperture;
wherein the vapor barrier is configured to open to permit the breathable gas to pass from the input aperture to the output aperture by an application of pneumatic pressure applied at the input aperture that exceeds the pressure at the output aperture;
wherein the vapor barrier is configured to close to prevent vapor passing from the output aperture to the input aperture with a pneumatic pressure applied at the output aperture that exceeds or is equal to pressure at the input aperture; and
wherein the vapor barrier is configured to transmit pressure changes that occur on a downstream side of the vapor barrier, through the vapor barrier, such that the pressure changes are detected by the pressure sensor when the vapor barrier is closed.

20. The device of claim 19, wherein the gas conduit further comprises an atmosphere access port, and wherein the vapor barrier is further configured to cover the atmosphere access port when the vapor barrier permits the breathable gas to pass from the input aperture to the output aperture.

21. The device of claim 20, wherein the vapor barrier is further configured to uncover the atmosphere access port when the vapor barrier prevents vapor passing from the output aperture to the input aperture.

22. A respiratory treatment apparatus having:
means for reducing conduit rainout within a gas conduit of the respiratory treatment apparatus, wherein the means for reducing conduit rainout is configured for selectively preventing vapor passing from a patient interface through the gas conduit to an input aperture of the gas conduit;
means for sensing pressure, the means for sensing pressure located upstream of the vapor barrier; and
means for conducting a breathable gas between the input aperture and an output aperture of the gas conduit;
wherein the means for reducing conduit rainout is configured to transmit pressure changes that occur on a downstream side of the means for reducing conduit rainout, through the means for reducing conduit rainout, such that the pressure changes are detected by the means for sensing pressure when the means for reducing conduit rainout is closed.

23. The respiratory treatment apparatus of claim 22, wherein the means for reducing conduit rainout within the gas conduit is also a means for normally sealing the gas conduit to prevent vapor passing from an output aperture of the gas conduit to the input aperture.

24. The respiratory treatment apparatus of claim 23, wherein the means for reducing conduit rainout within the gas conduit is also a means for permitting a breathable gas to pass from the input aperture to the output aperture by an application of pneumatic pressure applied at the input aperture that exceeds the pressure at the output aperture.

25. The respiratory treatment apparatus of claim 22, wherein the means for reducing conduit rainout within the gas conduit is also a means for allowing vapor to pass from the patient interface to atmosphere.

* * * * *